United States Patent

Nagasawa et al.

[11] Patent Number: 6,145,382
[45] Date of Patent: Nov. 14, 2000

[54] METHOD AND APPARATUS FOR MEASURING THE DAMPING CHARACTERISTICS OF A FRICTION MEMBER

[75] Inventors: Yuji Nagasawa; Masataka Osawa; Noriyasu Yamada; Fumio Ueda, all of Aichi-ken, Japan

[73] Assignee: Kabushiki Kaisha Toyota Chuo Kenkyusho, Aichi-gun, Japan

[21] Appl. No.: 09/137,696

[22] Filed: Aug. 21, 1998

[30] Foreign Application Priority Data

Sep. 19, 1997 [JP] Japan .................................. 9-273446

[51] Int. Cl.$^7$ ........................................... G01N 19/02
[52] U.S. Cl. ....................... 73/664; 73/9; 73/432.1; 73/DIG. 1
[58] Field of Search .............. 73/662, 664, 663, 73/579, 866.5, 432.1, DIG. 1, 11.05, 11.09, 7, 9

[56] References Cited

U.S. PATENT DOCUMENTS 5,107,448  4/1992  Nash ........................................ 364/556
5,996,395  12/1999  Nagasawa et al. ........................... 73/9
6,014,899  1/2000  Uhlig et al. ................................ 73/664

FOREIGN PATENT DOCUMENTS 5-126683   5/1993   Japan .
1485057    6/1989   U.S.S.R. .
1700439 A1 12/1991  U.S.S.R. .

*Primary Examiner*—Hezron Williams
*Assistant Examiner*—Rose M. Miller
*Attorney, Agent, or Firm*—Oblon, Spivak, McClelland, Maier & Neustadt, P.C.

[57] ABSTRACT

A method for measuring damping characteristics of a friction member include: relatively pressing a first member as a friction member to be measured against a second member, for relatively sliding with respect to a second member and vibrating, measuring vibration states of the pressed first and second members, and measuring variations in the vibration states of the pressed first and second members and measuring damping characteristics of the friction member to be measured against vibrations by comparing damped amounts based on the variations in the vibration states of the first and second members. The above method and an apparatus therefor enable detailed evaluations of friction member having high performance.

23 Claims, 5 Drawing Sheets

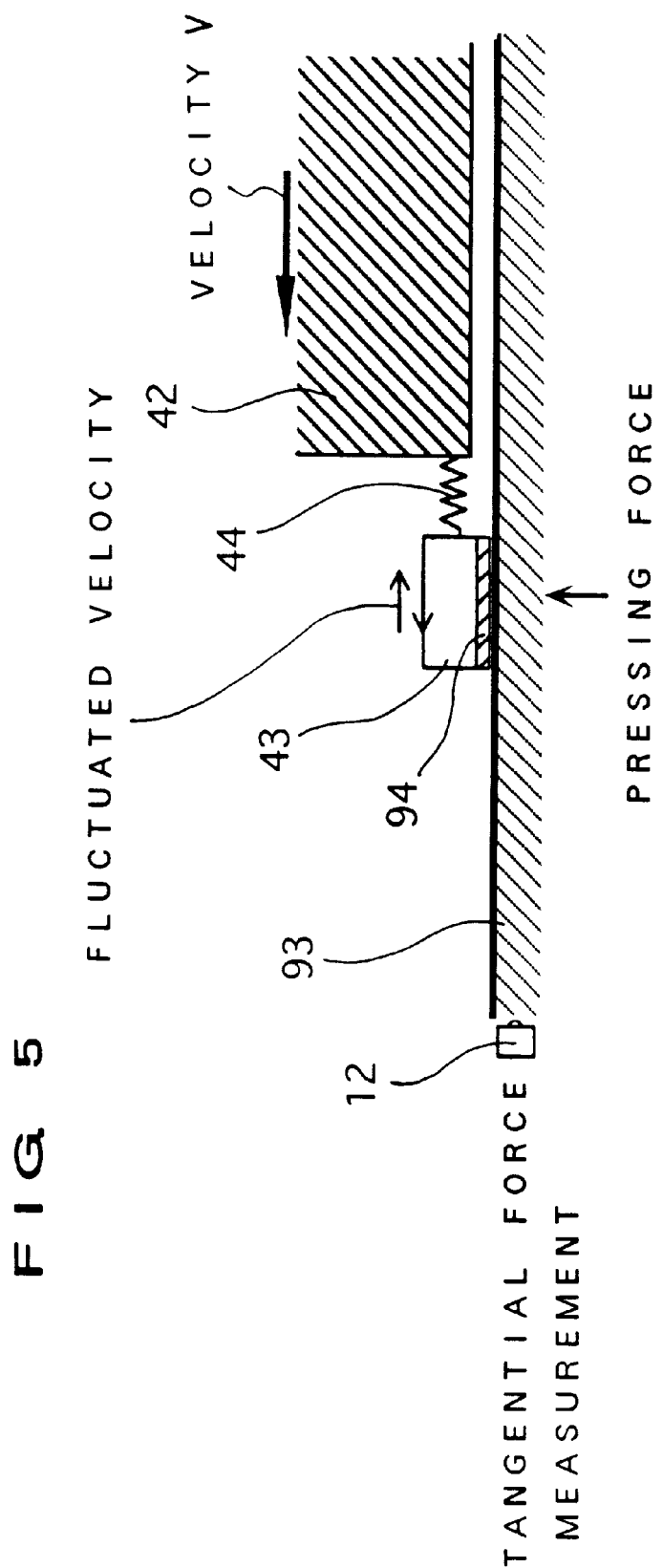

METHOD AND APPARATUS FOR MEASURING THE DAMPING CHARACTERISTICS OF A FRICTION MEMBER

BACKGROUND OF THE INVENTION

1. Field of the Invention

The present invention relates to a method and an apparatus for measuring the damping characteristics of a friction member with respect to vibration.

2. Description of the Related Art

In a conventional frictional vibration evaluation device (such as those described in Japanese Patent Application Laid-open Nos. 62-832 and 5-126683), a vibration system analogous to equipment to be practically used is disposed on a testing machine, and vibrations which are considered to actually arise in the equipment are simulated by the testing machine. Vibrations which would arise in actual equipment are predicted on the basis of the presence or absence of vibrations in the testing machine.

More specifically, in a testing machine such as that shown in FIG. 6, a brake shoe B, which serves as a friction member F made of friction materials, is attached to a main body H joined to a rotary shaft R which is rotated by a motor M, and the diameter of a torsion shaft T fixed to the main body H is reduced in order to facilitate the occurrence of judder. A torque meter TM is coupled to the torsion shaft T. Through use of the foregoing testing machine, a judder test is carried out in a test room without a car being subjected to test run.

The conventional testing machine allows only an evaluation as to whether or not the friction member F which is to be evaluated has the capability to cause frictional vibrations of a certain magnitude or higher. More specifically, the conventional testing machine determines only whether or not the friction member F causes frictional vibrations of such a magnitude as to exceed the inherent damping capability of the equipment.

The conventional frictional vibration evaluation device merely classifies friction members to be evaluated into two types, that is, a material which causes vibrations and a material which does not cause any vibrations, wherein only the damping capability of the evaluation device is used as a criteria for classification. The conventional frictional vibration evaluation device cannot evaluate the friction member in further detail.

To a certain extent, the conventional frictional vibration evaluation device can be used to evaluate the superiority or inferiority of the material on the basis of the magnitude of vibrations produced. However, the evaluation device can find only that a certain friction member causes frictional vibrations in the evaluation apparatus, i.e., the friction member has inferior vibration-suppressing capability, but cannot be used as an evaluation apparatus for friction members having superior damping characteristics.

In practice, variations exist in the rotational speed of the rotary shaft, and these variations cause vibrations that continue for a long period of time. The period of the continuation depends on the relationship between the magnitude of damping or vibration-suppressing characteristics and that of excitation characteristics of an equipment and a friction member. Various variations exist in a machine to be actually used, and hence vibrations are apt to arise. Vibrations such as judder are phenomena in which vibrations occur at the eigenfrequency (natural frequency) of the equipment and continue for a long period of time. The vibrations occurring at the eigenfrequency are characterized by the phenomenon that the greater the damping in the vibration system, the smaller the vibration amplitude caused by vibration force imparted to the vibration system, thereby preventing the vibrations from becoming greater. In order to prevent vibrations from continuing for a long period of time in every situation, the friction member itself must have no excitation characteristics and must have high resistance, or high damping performance against external vibrations. The aforementioned conventional frictional vibration evaluation device performs an evaluation only as to whether or not the friction member causes vibrations, but is incapable of evaluating the friction member with regard to given vibrations which are important factors in practical use.

SUMMARY OF THE INVENTION

It is a general object of the present invention to provide a method and an apparatus for measuring the damping characteristics of a friction member which enables further detailed evaluations in addition to rough classification of friction members in light of generation of vibrations and superiority/inferiority evaluation.

It is another object of the present invention to provide a method and an apparatus for measuring the damping characteristics of a friction member which enables use as an evaluation device for a friction member having superior damping characteristics.

It is still another object of the present invention to provide a method and an apparatus for measuring the damping characteristics of a friction member which evaluate a friction member having high performance.

It is a further object of the present invention to provide a method and an apparatus for measuring the damping characteristics of a friction member comprising the steps of: relatively pressing a first member as a friction member to be measured against a second member, for relatively sliding and vibrating the first member with respect to the second member, and measuring vibrational variations of at least one of the first and second members by the pressing to obtain damped amounts based on the vibrational variations, and measuring damping characteristics of the friction member against vibrations based on the damped amounts.

It is a still further object of the present invention to provide a method and an apparatus for measuring the damping characteristics of a friction member wherein the step of measuring the vibrational variations comprises a step of measuring variations in vibration states of the first member before and after the pressing.

It is a yet further object of the present invention to provide a method and an apparatus for measuring the damping characteristics of a friction member wherein the step of measuring the vibrational variations comprises a step of measuring variations in vibration states of the first member caused by the pressing.

Namely in the measuring step, the variations in the vibration states of the first member after the pressing are measured.

It is a yet further object of the present invention to provide a method for measuring the damping characteristics of a friction member wherein the damping characteristics of a friction member are measured by the steps of: relatively pressing a first member as a friction member to be measured, for relatively sliding with respect to a second member and vibrating, against the second member; measuring vibration states of the pressed first or second member to be measured; and measuring variations in the vibration states of the pressed first or second member to be measured due to pressing by the pressing mechanism, and measuring the damping characteristics of the friction members against vibrations by comparing damped amounts based on the vibration in the vibration states of the first and second members.

It is another object of the present invention to provide a method for measuring the damping characteristics of a friction member comprising the steps of: relatively pressing a first member as a friction member to be measured, for relatively sliding with respect to a second member and vibrating, against the second member, measuring vibration states of the pressed first and second members, and measuring variations in the vibration states of the pressed first and second members and measuring damping characteristics of the friction members to be measured against vibrations by comparing damped amounts based on the variations in the vibration states of the first and second members.

It is a further object of the present invention to provide an apparatus for measuring the damping characteristics of a friction member comprising: a drive mechanism for relatively sliding a first member, as a friction member to be measured, against a second member; a vibration generation mechanism for vibrating the first member; a pressing mechanism for relatively pressing the first member against the second member; a first measuring unit for measuring a vibration state between the first and second members; and a second measuring unit for measuring vibrational variations of at least one of the first and second member by the pressing to obtain damped amounts based on the vibrational variations and for measuring damping characteristics of the friction member against vibrations by comparing damped amounts based on the variations in the vibration states of the first and second members.

It is a yet further object of the present invention to provide a method for measuring the damping characteristics of a friction member comprising the steps of: relatively pressing, through use of a pressing mechanism, a first member to be measured, which is a friction member made of friction materials or a metallic material to be contacted with the friction member made of the friction materials, against a second member to be measured, which is made of the friction material, the second member rotating or displacing relative to the first member in a sliding manner, and free or forced vibrations being imparted to the first member; measuring the vibration state of the first or second member to be measured through use of a vibration measurement section; and measuring variations in the vibration state of the first or second member to be measured due to pressing by the pressing mechanism, and comparing damped amounts of the vibration in order to measure the damping characteristics of the friction members against vibrations.

Under the method and the apparatus for measuring the damping characteristics of a friction member having the aforementioned configuration according to the present invention, the damping characteristics of friction members are measured by the steps of: relatively pressing, through use of a pressing mechanism, a first member as a friction member to be measured, which is made of the friction materials, against the second member to be measured, which is made of the friction material, the second member rotating or displacing relative to the first member in a sliding manner, and free or forced vibrations being imparted to the second member; measuring, through use of an oscillation measurement section, the vibration state of the first or second member to be measured; and measuring variations in the vibration state of the first or second member to be measured due to pressing by the pressing mechanism, and comparing damped amounts of the vibration in order to measure the damping characteristics of the friction member against vibrations.

Under the foregoing method and the apparatus for measuring the damping characteristics of the friction member according to the present invention, which is operated in the manner as mentioned previously, the damping characteristics of the friction member with respect to vibration are measured by comparison of amounts of damping caused by variations in the vibration state of the friction members which variations are caused by pressing by the pressing mechanism. As a result, the present invention has the advantage of enabling further detailed evaluations in addition to rough classification of friction members in light of generation of vibrations and superiority/inferiority evaluation, and enabling use of the device as an evaluation device for friction members having superior damping characteristics, thereby making it possible to evaluate friction members having high performance.

BRIEF DESCRIPTION OF THE DRAWINGS

FIG. 5 is a plan view showing a device which practices a method of measuring the damping characteristics of a friction member according to a fourth embodiment of the present invention.

DETAILED DESCRIPTION OF THE PREFERRED EMBODIMENTS

By reference to the drawings, preferred embodiments of the present invention will be described.

(First Embodiment)

Figure 1:
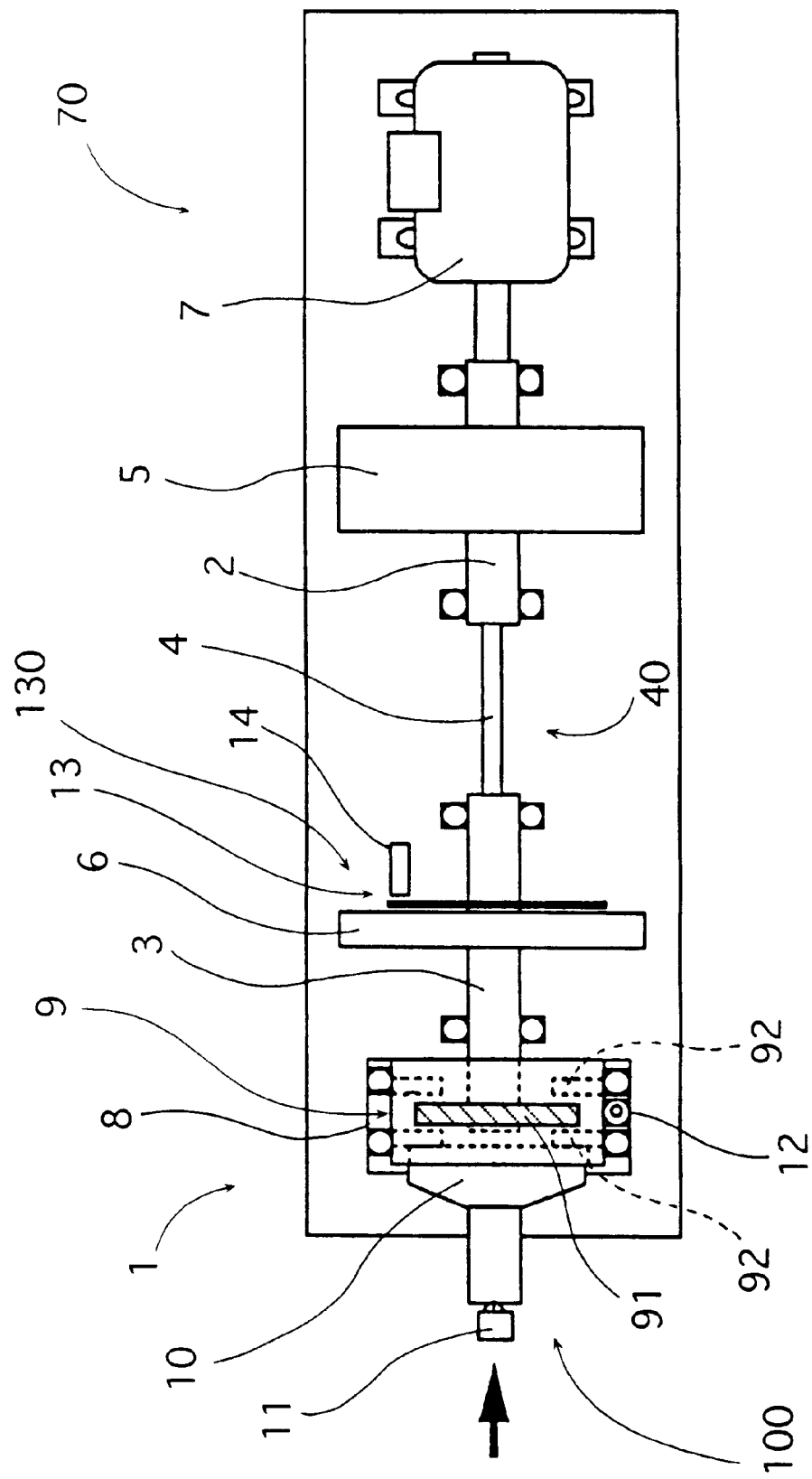
FIG. 1 is a plan view showing a device which practices a method of measuring the damping characteristics of a friction member according to a first embodiment of the present invention.

As shown in FIG. 1, under a method and an apparatus for measuring the damping characteristics of a friction member according to a first embodiment of the present invention, a friction member 92 as a second member, which constitutes a member 9 made of a frictional material to be measured, is pressed, by a pressing mechanism 100, against a rotary disk 91 as a first member, which also constitutes the member 9 to be measured. The rotary disk 91 rotates and is imparted with free or forced vibrations from a vibration generation section 40. The state of vibration of the rotary disk 91 and the friction member 92, both of which constitute the member 9 made of a frictional material to be measured, is measured by a vibration measurement section 130. There are measured variations in the vibration state of the member 9 caused by the pressing action of the pressing mechanism 100. The damping characteristics of the friction member with regard to vibration are determined by comparison of the amounts of damping in vibrations.

As shown in FIG. 1, a rotary drive section 70 comprises a motor 7 mounted on a table 1 and a first rotary shaft 2 which is joined to and rotatively actuated by the motor 7 and is supported at both ends.

As shown in FIG. 1, the vibration generation section 40 comprises a first flywheel 5 which has a large inertia and is attached to the first rotary shaft 2; a second flywheel 6 which has a small inertia and is attached to a second rotary shaft 3 supported at both ends; and a small-diameter shaft 4 which connects the first rotary shaft 2 to the second rotary shaft 3 and has a diameter sufficiently smaller than that of the first and second rotary shafts. The vibration generation section 40 constitutes a torsional vibration system.

As shown in FIG. 1, a frictional characteristic measurement section 8 comprises a pair of friction members 92, which constitute the member 9 to be measured and are disposed to either side of the rotary disk 91. The rotary disk 91 is a friction member made of the friction materials and also constitutes the member 9 to be measured, and is attached to one end of the second rotary shaft 3. Of the pair of friction members 92 that are spaced away from and facing each other, one friction member is provided so as to be movable in the axial direction so that the rotary disk 91 may be sandwiched between the pair of friction members 92.

The rotary disk 91 and the pair of friction members 92, which are arranged so as to sandwich the rotary disk 91 between them, are made from the same friction material whose damping characteristics are to be measured.

As shown in FIG. 1, the pressing mechanism 100 comprises a piston 10 which presses one of the pair of friction members 92 in the axial direction (i.e., in the rightward direction in FIG. 1); a pressing load cell 11 interposed between the piston 10 and a drive source (not shown) and which measures a pressing load; and a tangential load cell 12 for measuring a tangential force caused by the rotary disk 91 and the frictional members 92.

As shown in FIG. 1, the vibration measurement section 130 comprises a rotary member 13 which is formed integrally with the rotary disk 91 serving as the member to be measured and has a plurality of slits radially formed therein at given angles; and a sensor 14 which detects the number of revolutions and rotational variations as the vibration state of the rotary member 13.

Under the method and apparatus for measuring the damping characteristics of the friction member according to the first embodiment through use of the apparatus having the foregoing configuration, the motor 7 mounted on the table 1 rotates the first rotary shaft 2 having the first flywheel 5 attached thereto.

The first rotary shaft 2 rotates the second rotary shaft 3 having the flywheel 6 attached thereto via the small-diameter shaft 4 connecting the first rotary shaft 2 to the second rotary shaft 3. As a result, the rotary disk 91 that serves as the member 9 to be measured and is attached to one end of the second rotary shaft 3 is rotated within the frictional characteristic measurement section 8.

The friction member 92 also constituting the member 9 to be measured is disposed in the frictional characteristic measurement section 8 and is pressed, by means of the piston 10 of the pressing mechanism 100, against the rotary disk 91.

At this time, the load cell 11 measures a pressing load, and the tangential load cell 12 measures the tangential force imparted by the member 9. The sensor 14 detects the number of revolutions of the rotary member 13 having the slits formed therein and measures the number of revolutions of the second rotary shaft 3.

The damping characteristics of the friction member of the member 9 to be measured are evaluated by determination of the extent to which the vibrations occurring in the rotary shaft 3 before commencement of the test are damped after the friction members 92 have been pressed against the rotary disk 91.

It is effective for the vibration generation section 40 that serves as means for causing vibrations in the second rotary shaft 3 before the test to impart the braking force produced by the friction members 92 and the rotary disk 91 to the second rotary shaft 3 in accordance with the torsional frequency of the torsional vibration system formed from the first and second flywheels 5, 6 and the small-diameter shaft 4.

Even in a case where the vibrations in the rotary shaft 3 are increased after the friction members 92 have been pressed against the rotary disk 91, the damping characteristics of the friction member can be evaluated from the extent to which the vibrations are increased, as in the case where the vibrations are damped. The damping coefficient of a friction member is usually obtained by the following expression.

$$\text{Vibration } x = A * e^{-rt} \sin(wt + \emptyset)$$

where

A: amplitude;

r: damping coefficient;

w=2πf wherein f: frequency; and

Ø: phase.

For example, the vibration x specifically represents a velocity variation or a torque variation.

Figure 2:
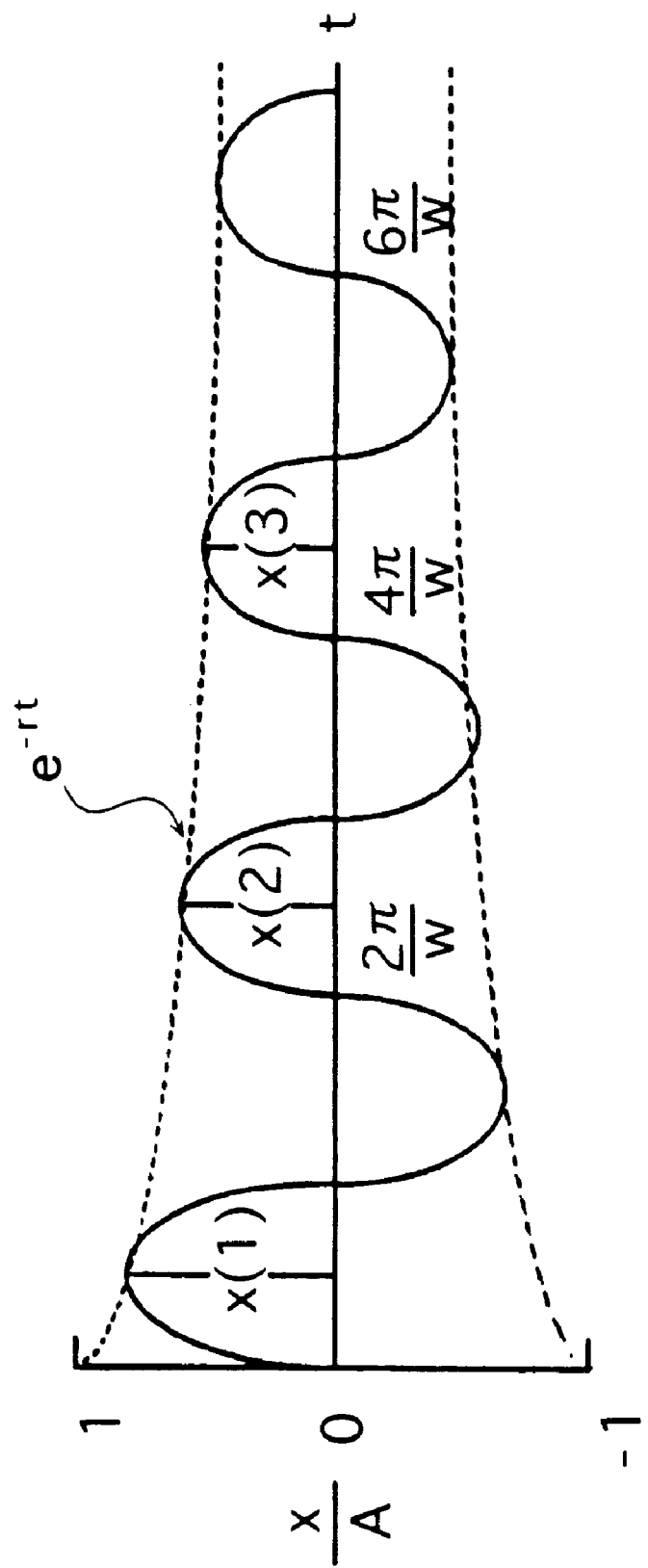
FIG. 2 is a diagrammatic representation showing vibrations measured by the apparatus according to the first embodiment.

FIG. 2 shows a curve plotting the damping in vibration, where the phase Ø is zero.

Each of intersections between the curve represented by $e^{-rt}$ (designated by a broken line in FIG. 2) and a vibration curve appears at a position shifted slightly rightward from the point representing the respective maximum value. However, when the damping coefficient "r" takes on a small value, an intersection between the curve $e^{-rt}$ and the vibration curve is deemed to be equal to the maximum value x (n). The interval between the maximum values is a cycle T (=2π/w) and is expressed as follows:

$$x(1)/x(2) = x(2)/x(3) = e^{+rT}$$

therefore, $$r = (1/T) \ln\{x(n)/x(n+1)\}.$$

When the damping coefficient "r" takes on a large value, vibrations are damped immediately. Therefore, a friction member having a large damping coefficient "r" is evaluated as a material having superior vibration resistance.

The method and the apparatus for measuring the damping characteristics of a friction member in accordance with the first embodiment, which is practiced in the aforementioned manner, has the advantage of being able to measure the damping characteristics of a friction member with regard to vibration by comparing the amounts of damping in vibration caused by variations in the vibration state of the member 9 due to the press of a pressing mechanism 100.

Accordingly, the method and the apparatus yield the advantage of enabling evaluation of a friction member in terms of viewpoints other than the possibility of vibration occurrence by comparing the amounts of damping caused by the variations in the vibration state of the member 9.

Further, the method and the apparatus for measuring the damping characteristics of a friction member in accordance with the first embodiment has the advantage of enabling an evaluation device for friction members having superior damping characteristics, thereby making it possible to evaluate friction members having superior performance.

Moreover, since the method and the apparatus for measuring the damping characteristics of a friction member in accordance with the first embodiment enables evaluation of friction members having superior damping characteristics, it becomes possible to select and develop a friction member having superior damping characteristics.

(Second Embodiment)

Figure 3:
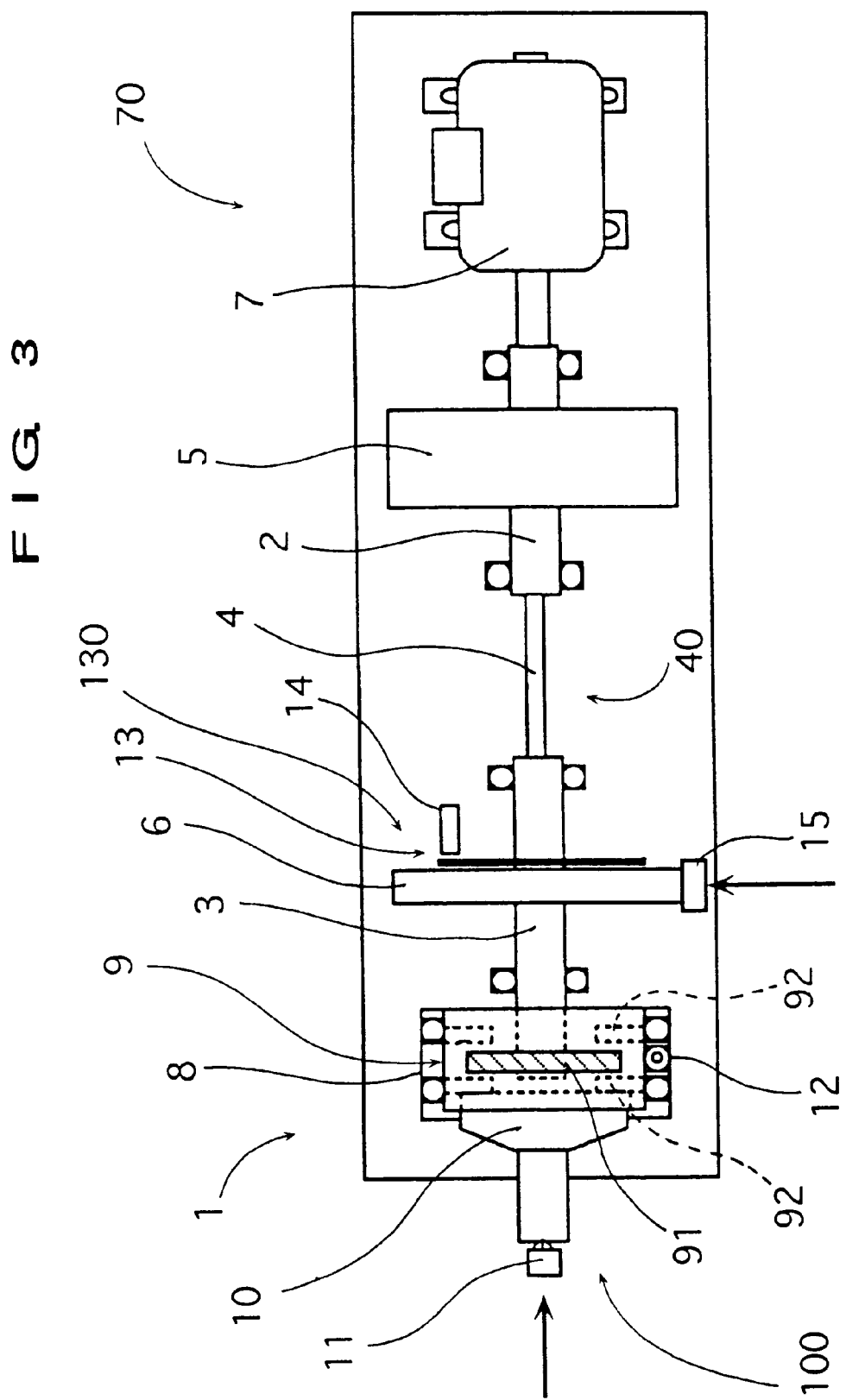
FIG. 3 is a plan view showing a device which practices a method of measuring the damping characteristics of a friction member according to a second embodiment of the present invention.

As shown in FIG. 3, a method and an apparatus for measuring the damping characteristics of a friction member in accordance with a second embodiment of the present invention is different from the method and the apparatus described in the first embodiment in that braking force is imparted directly to the second rotary shaft 3. An explanation will chiefly describe the difference.

Through use of a brake 15, braking force is imparted directly to the second small-capacity flywheel 6 attached to the second rotary shaft 3, which is supported at both ends, whereby braking force is imparted to the vibrations that have developed in the second rotary shaft 3 prior to the test.

Under the method and the apparatus for measuring the damping characteristics of the friction member in accordance with the second embodiment, which employs the foregoing configuration, braking force is imparted to the vibrations that have developed in the second rotary shaft 3 before the test, by imparting the braking force directly to the second rotary shaft 3 by means of the brake 15. Accordingly, the method and the apparatus yield the advantage of stably producing vibrations in the rotary shaft 3 by control of the braking force of the brake 15.

(Third Embodiment)

Figure 4:
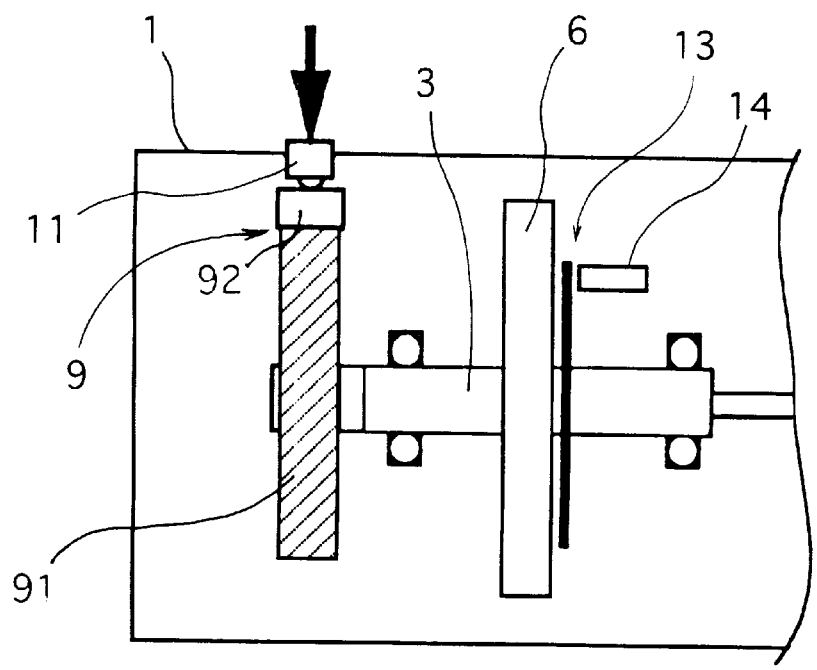
FIG. 4 is a plan view showing a device which practices a method of measuring the damping characteristics of a friction member according to a third embodiment of the present invention.
Figure 6:
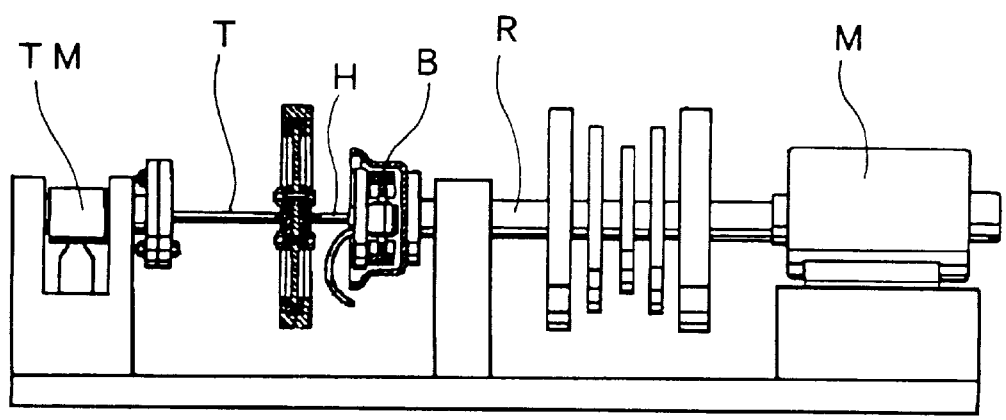
FIG. 6 is a partially sectioned front view showing the entirety of a conventional frictional vibration evaluation device.

As shown in FIG. 4, a method and an apparatus for measuring the damping characteristics of a friction member in accordance with a third embodiment of the present invention is different from the method described in the first embodiment in that the friction member 92 constituting a member 9 to be measured are pressed against the outer peripheral wall of the rotary disk 91 also constituting the member 9 to be measured. An explanation will chiefly describe the difference.

As shown in FIG. 4, the pressing mechanism 100 is configured so as to impart the pressing force exerted from a drive source (not shown) in a radially inward direction to the friction member 92 and the outer peripheral wall of the rotary disk 91 via the pressing load cell 11.

Under the method and the apparatus for measuring the damping characteristics of a friction member in accordance with the third embodiment, which employs the foregoing configuration, the friction member 92 is pressed against the outer peripheral wall of the rotary disk 91 via the pressing load cell 11 by means of the pressing force exerted in a radially-inward direction. Accordingly, the friction member 92 comes into sliding contact with the outer peripheral wall of the rotary disk 91 in a circumferential direction, thereby resulting in a uniform peripheral speed at every location. As a result, there is yielded the advantage of enabling the sliding action of the friction member to be handled as an approximate linear motion.

Further, under the method and the apparatus for measuring the damping characteristics of a friction member in accordance with the third embodiment, since the sliding action of the friction member 92 with respect to the outer peripheral wall of the rotary disk 91 in the circumferential direction can be handled as an approximate linear motion, there is yielded the advantage of enabling measurement of the damping characteristics of the friction member by means of a compact device.

(Fourth Embodiment)

As shown in FIG. 5, a method and an apparatus for measuring the damping characteristics of a friction member in accordance with a fourth embodiment of the present invention is different from the method described in the first embodiment in that a friction member 94 which constitutes a member 9 to be measured and is provided on a plane friction member 93 is linearly moved with respect to the friction member 93 also constituting the member 9 to be measured. An explanation will chiefly describe the difference.

The friction member 94 is positioned on the plane friction member 93 and is attached to a lower surface of a member 43 joined via a spring 44 to a member 42 which travels linearly at a given speed. The friction member 94 is arranged so as to move over the plane friction member 93 at a given fluctuated velocity.

A pressing force is exerted on the plane friction member 93 in an upward direction in the drawing by means of the pressing mechanism, and the tangential load cell 12 is provided on the side wall of the plane friction member 93 for measuring tangential force.

Under the method and the apparatus for measuring the damping characteristics of the friction member in accordance with the fourth embodiment, which employs the foregoing configuration, the friction member 94 linearly travels over the plane friction member 93 at a given fluctuated velocity. Therefore, the method and apparatus yield the advantage of enabling measurement, with regard to vibration, of the damping characteristics of the friction member traveling linearly.

Further, under the method and the apparatus for measuring the damping characteristics of a friction member in accordance with the fourth embodiment, since the damping characteristics of the friction member traveling linearly can be measured with respect to vibration, there is yielded the advantage of enabling evaluation and development of the friction member to be used in a linearly-traveling state.

The preferred embodiments of the present invention, as herein disclosed, are taken as some embodiments for explaining the present invention. It is to be understood that the present invention should not be restricted by these embodiments and any modifications and additions are possible so far as they are not beyond the technical idea or principle based on descriptions of the scope of the patent claims.

What is claimed is:

1. A method for measuring damping characteristics of a friction member comprising the steps of:

relatively pressing a first member as a friction member to be measured against a second member, for relatively sliding and vibrating said first member with respect to said second member, and measuring vibrational variations of at least one of said first and second members by said pressing to obtain damped amounts based on said vibrational variations, and measuring damping characteristics of said friction member against vibrations based on said damped amounts, wherein said step of measuring said vibrational variations comprises a step of measuring variations in vibration states of said first member before and after said pressing.

2. A method for measuring damping characteristics of a friction member according to claim 1, wherein
said step of measuring said vibrational variations comprises a step of measuring variations in vibration states of said first member caused by said pressing.

3. A method for measuring damping characteristics of a friction member according to claim 2, wherein
said second member is a friction member to be measured.

4. A method for measuring damping characteristics of a friction member according to claim 3, wherein
said first member comprises a rotary disk relatively rotating with respect to said second member.

5. A method for measuring damping characteristics of a friction member according to claim 3, wherein
said first member comprises a linearly moving member relatively moving in one direction with respect to said second member.

6. A method for measuring damping characteristics of a friction member according to claim 3, wherein
said first member vibrates on a free vibration mode.

7. A method for measuring damping characteristics of a friction member according to claim 3, wherein
said first member vibrates on a forced vibration mode.

8. A method for measuring damping characteristics of a friction member according to claim 1, wherein
said step of measuring damping characteristics of said friction member comprises a step of comparing the amounts of damping caused by the variations in the vibration state of said first member before and after said pressing.

9. An apparatus for measuring damping characteristics of a friction member comprising:
a drive mechanism for relatively sliding a first member, as a friction member to be measured, against a second member;
a vibration generation mechanism for vibrating said first member;
a pressing mechanism for relatively pressing said first member against said second member;
a first measuring unit for measuring a vibration state between said first and second members; and
a second measuring unit for measuring for measuring vibrational variations of at least one of said first and second member by said pressing to obtain damped amounts based on said vibrational variations and for measuring damping characteristics of said friction member against vibrations by comparing damped amounts based on the variations in the vibration states of said first and second members, wherein
said second measuring unit comprises means for comparing the amounts of damping caused by the variations in the vibration state of said first member before and after said pressing.

10. An apparatus for measuring damping characteristics of a friction member according to claim 9, wherein
said second member is made of a friction member to be measured.

11. An apparatus for measuring damping characteristics of a friction member according to claim 10, wherein
said first member comprises a rotary disk relatively rotating with respect to said second member.

12. An apparatus for measuring damping characteristics of a friction member according to claim 11, wherein
said drive mechanism comprises a rotary drive mechanism for rotating said rotary disk.

13. An apparatus for measuring damping characteristics of a friction member according to claim 12, wherein
said vibration generation mechanism further comprises a free vibration mechanism for vibrating said rotary disk on a free vibration mode.

14. An apparatus for measuring damping characteristics of a friction member according to claim 12, wherein
said vibration generation mechanism comprises a forced vibration mechanism for vibrating said rotary disk on a forced vibration mode.

15. An apparatus for measuring damping characteristics of a friction member according to claim 14, wherein
said second member comprises a pair of annular plates positioned at a predetermined gap, sandwiching said rotary disk therebetween.

16. An apparatus for measuring damping characteristics of a friction member according to claim 15, wherein
said pressing mechanism comprises a piston for pressing one of the pair of annular plates.

17. An apparatus for measuring damping characteristics of a friction member according to claim 16, wherein
said first measuring unit comprises a rotary member, having a plurality of slits, formed integrally with said rotary disk and a sensor for detecting the number of revolutions and rotational variations of said rotary disk.

18. An apparatus for measuring damping characteristics of a friction member according to claim 17, wherein
said vibration generation mechanism comprises a torsional vibration system which comprises a first flywheel having a high capacity, a second flywheel having a small capacity connected to said rotary disk, and a torsion shaft having a small diameter and connecting said first and second flywheels.

19. An apparatus for measuring damping characteristics of a friction member according to claim 18, wherein
said vibration generation mechanism further comprises a brake for pressing an outer peripheral wall of said second flywheel by a braking force.

20. An apparatus for measuring damping characteristics of a friction member according to claim 15, wherein
said pressing mechanism comprises an external pressing mechanism for pressing said second member of said friction member to an outer peripheral wall of said rotary disk through a load cell.

21. An apparatus for measuring damping characteristics of a friction member according to claim 10, wherein
said first member comprises a linearly moving friction member relatively moving in one direction with respect to a plane friction member as said second member.

22. An apparatus for measuring damping characteristics of a friction member according to claim 21, wherein
said first member is connected through a spring to a travel member for traveling linearly at a given fluctuated speed.

23. An apparatus for measuring damping characteristics of a friction member according to claim 22, wherein
said pressing mechanism comprises an upward pressing mechanism for exerting a pressing force on said plane friction member in an upward direction thereof, and
a tangential load cell for measuring tangential force is provided on one side wall of said plane friction member.

* * * * *